United States Patent [19]

Spicer et al.

[11] Patent Number: 5,106,649
[45] Date of Patent: Apr. 21, 1992

[54] METHOD FOR IMPROVING THE BULK FLOW PROPERTIES OF PESTICIDE TREATED PLANT SEEDS USING A NON CROSSLINKED POLYDIMETHYLSILOXANE AS A LUBRICANT THEREFORE

[75] Inventors: Andrew R. Spicer, Sandy; Patrick J. Mulqueen, Abingdon, both of England

[73] Assignee: DowElanco, Indianapolis, Ind.

[21] Appl. No.: 496,564

[22] Filed: Mar. 20, 1990

[30] Foreign Application Priority Data

Mar. 22, 1989 [GB] United Kingdom ............... 8906588

[51] Int. Cl.⁵ .............................................. A01G 5/06
[52] U.S. Cl. ........................................ 427/4; 427/212; 427/214; 47/57.6
[58] Field of Search .............. 427/4, 212, 407.1, 214, 427/200, 299; 47/57.6

[56] References Cited

U.S. PATENT DOCUMENTS

| | | | |
|---|---|---|---|
| 3,808,740 | 5/1974 | Porter | 47/58 |
| 4,172,904 | 10/1979 | Young et al. | 427/4 |
| 4,244,849 | 1/1981 | Saam | 428/447 |
| 4,632,847 | 12/1986 | Lomasney et al. | 427/154 |
| 4,720,521 | 1/1988 | Spielvogel et al. | 427/387 |
| 4,729,190 | 3/1988 | Lee | 47/57.6 |
| 4,753,035 | 6/1988 | Ryan et al. | 47/57.6 |

Primary Examiner—Michael Lusignan
Assistant Examiner—Diana L. Dudash
Attorney, Agent, or Firm—S. Preston Jones

[57] ABSTRACT

A method for substantially improving the bulk flow properties of pesticide-treated plant seeds is disclosed. The seeds are treated with low levels of a polydimethylsiloxane lubricant which is applied either to seeds that have already been treated with a pesticidal substance or to seeds simultaneously with a pesticidal substance. The polydimethylsiloxane lubricant can be applied either by coapplication from separate compositions or by the application of a composition containing both the pesticidal substance and the polydimethylsiloxane lubricant.

10 Claims, No Drawings

METHOD FOR IMPROVING THE BULK FLOW PROPERTIES OF PESTICIDE TREATED PLANT SEEDS USING A NON CROSSLINKED POLYDIMETHYLSILOXANE AS A LUBRICANT THEREFORE

FIELD OF INVENTION

This invention relates to concerns a composition for the treatment of agricultural seeds with pesticides, in particular with fungicides and insecticides. The treatment of seeds with pesticides can be a very efficient method of applying pesticides to a crop, where a seed is susceptible to attack by soil borne, seed borne, and foliar pathogens, or when the pesticide can move freely within the seedling or young plant, to protect the emerging plant against insect or fungal attack.

BACKGROUND OF INVENTION

Various methods are employed for the application of pesticides to seeds, for example dusting them, and applying them with aqueous and non-aqueous solutions and suspensions.

The effectiveness of dusts is dependent upon the ability of the seed to retain a sufficient amount of the dust to protect the seed. Adhesion of pesticidal dust to seeds is usually poor, and the use of dust is therefore undesirable. Also because of the possibility of environmental hazard, due to toxicity, use of dusts is limited.

Non-aqueous liquid pesticidal compositions are an improvement over dusts but generally require an atomizing system in order to produce an efficient distribution f the composition on the seed. Such systems often require the use of potent organic solvents such as glycols, dimethyl formamide, or aromatic solvents to dissolve the pesticide and allow efficient distribution of the pesticide on the seed. Such solvents are often toxic in their own right and can increase the dermal toxicity of the pesticide thereby increasing the health risk to seed application personnel and can cause corrosion in the application equipment. The solvents can also have adverse effects on the germination efficiency of the treated seed. These factors are all aspects which are less than desirable in a seed treatment composition.

For these reasons aqueous based seed treatment systems are the most preferred, being dust-free in the application stage and having little or no non-aqueous solvents. Much research has therefore been expended in devising aqueous based formulations of pesticides suitable for application to seeds.

It is highly desirable that an aqueous pesticide formulation applied to seed should present the pesticide in an optimum manner to perform its function, render the seed such that a user knows it is treated with a pesticide and allow the seed to perform normally in all physical and biological aspects.

The pesticide composition should also be evenly distributed about the seed in a homogeneous manner to protect all the seed from attack, especially by a fungal pathogen. Such treated seed should also retain a high percentage of the applied pesticide, not allowing the pesticide to drop off the seed or to be rubbed off by the bulk flow properties of treated seed. This rubbing off of pesticide causes again the undesirable creation of dust as well as reducing the pesticide loading on the seed and rendering the seed more vulnerable to attack than seed retaining the pesticide completely.

While normal aqueous pesticide formulations can indeed be prepared by those skilled in the art to make the seed visible by addition of a dye or pigment and such that the pesticide can be evenly distributed about the seed, it is also recognized that typical aqueous pesticide compositions can affect the seed such that the physical and biological properties of the treated seed are adversely affected. This effect is especially so in the critical physical property of bulk seed flow (in processing equipment, seed hoppers and seed drills). Typical aqueous pesticide compositions also fail to retain the full amount of applied pesticide. This failure is especially apparent with complicated pesticide mixtures of solids which are applied at relatively high volumes to seed. This failure results in poor retention of pesticide on seed, dust production and build up of possible deposits in and even blockage of, seed drilling equipment with consequent loss of productivity.

Much research effort has been spent in attempts to develop improved aqueous based pesticide treatment systems which do not suffer from the above defects. A number of proposals have been made. However, in order to produce a seed coating of a pesticide on a seed having all or most of the desired properties, such prior proposals have required drying equipment to remove the excess water added during the application process.

The prior art compositions also include relatively high levels of added polymers. It can be easily ascertained by examination of the products available in commerce, that such compositions still do not entirely eliminate the dust production caused by poor retention of pesticide. Drying equipment is also an expensive capital investment for a seed treatment merchant which represent a very undesirable economic aspect of the use of such systems.

There exists, therefore, a need for a method of treating seeds with an aqueous based pesticide composition which 1) does not require the use of expensive drying equipment yet which effectively retains the pesticide efficiently on the surface of the seed, 2) allows the pesticide to be evenly distributed about the seed, and which preferably marks the seed, 3) allows the seed to perform in all physical and biological aspects as though it has no pesticide attached to it, and 4) permits the pesticide to be applied quickly and efficiently through conventional seed treatment machinery.

A number of aqueous pesticidal seed treatment formulations are commercially available, but most suffer from the undesirable side-effect that they adversely affect the bulk flow properties of the treated seed. This bulk flow property is of enormous commercial importance, because the seed must be handled in seed hoppers and seed drills, which, in general, require good flow properties which are of great commercial importance for any pesticide-treated seed.

It has been found that certain commercially available seed treatment compositions can decrease the rate of flow of the bulk seed in a seed drill by as much as 30 percent.

Most types of seed treatment machinery currently available in the U.K. use the rotary atomizer disc principle. In this system grain falls in a curtain peripheral to a rapidly spinning disc. A liquid formulation is fed, via metering pumps, on to the disc and forms a film which moves to the disc edge by centrifugal action. It leaves the disc as thin filaments or sheets which disintegrate into a mist of droplets. The gains fall through the mist picking up a uniform dose of the formulation.

Virtually all these types of machine have augers fitted to them which improve the redistribution capabilities of flowable formulations.

The seed treatment machine meters the seeds in to the atomizer chamber either continuously or on a batch basis, with the throughput being dependent on both the type of grain being treated and the type of product being applied.

SUMMARY OF THE INVENTION

Surprisingly, it has now been found that the bulk flow properties of pesticide-treated seeds can be substantially improved by the application to the seeds of low levels of a polydimethylsiloxane lubricant (hereinafter referred to as PDMS). The PDMS lubricant is applied as an aqueous emulsion, in an amount of from 0.001 to 0.2 percent (calculated as solids), based on the weight of the untreated seeds, and can be applied either to seeds which have already been treated with a pesticidal substance at a desired dosage, or preferably, can be applied to the seeds simultaneously with a pesticidal substance, either by coapplication from separate compositions (e.g. using separate feed lines to the atomizer), or else by the application of a composition containing both the pesticidal substance and the polydimethylsiloxane.

The use of polydimethylsiloxanes in a seed coating is known, for example from U.S. Pat. No. 4,753,035. The coatings used in this U.S. patent however are supplied to the seeds, not for their lubrication properties, but to protect the seeds, and promote germination. The reference discloses the use of crosslinkable silicon-containing materials, which are crosslinked on the surface of the seeds, to produce a porous crosslinked coating, permeable to water vapor and oxygen. Because the polydimethylsiloxanes are intended to protect the seeds, they are applied as relatively thick coatings, for example at application rates of approximately 6 percent or so, based on the weight of the seeds. These is no suggestion in this patent that the use of polydimethylsiloxanes at levels very much lower than those suggested for protective coatings can improve substantially the flow characteristics of pesticide-treated seeds.

Accordingly, the present invention provides a method for applying a pesticidal composition for treating seeds, which method comprises treating seeds with an effective amount of a pesticidal substance, and with a lubricant of from 0.001 percent to 0.2 percent based on the weight of the untreated seeds, which lubricant is a non-crosslinkable polydimethylsiloxane, and which composition has been applied to the seeds as an aqueous emulsion thereof.

The pesticidal substance and the PDMS are preferably applied in the form of a single composition comprising from 0.5 to 30 percent of the pesticidal substance, and from 1 to 30 percent of the PDMS. In an alternative preferred embodiment, the pesticidal substance and the PDMS are applied simultaneously to the seeds from separate feed pipes to the spray disc such that the PDMS is applied at a rate of from 0.001 to 0.2 percent (based on the untreated seed). and the pesticide is applied at a rate of from 0.002 to 3.0 percent, based on the untreated seed.

The term "non-crosslinkable" as used herein in connection with the PDMS is intended to mean that the PDMS does not crosslink on the surface of the seeds to provide a solid, non-flowing material, as do the materials employed in U.S. Pat. No. 4,753,035, but instead remains in a liquid or glassy state when applied to the seeds to promote slip between the seeds.

The PDMS is applied in the form of an aqueous emulsion. which preferably also comprises a film-forming polymer, for example, a polyalkylene glycol (such as polyethylene glycol), an alkyd resin, a polyvinyl alcohol, a polyvinyl pyrrolidone, a polyvinyl pyrrolidone/-vinyl acetate copolymer, a styrene or ethylene/acrylic acid copolymer a methyl cellulose, a film forming latex, a sucrose ester such as sucrose laurate, an ethyl cellulose or hydroxypropyl cellulose, a maleic anhydride/vinyl ether copolymer, a polyacrylate or polymethacrylate or similar film forming polymer. It may also contain a coloring agent, for example, a dye or a pigment in an amount sufficient to color the treated seeds so as to indicate clearly to the user coating has been applied.

Such an emulsion may also contain other components such as dispersants, solvents to improve compatibility of the component such as glycols, N-methyl pyrrolidone anti-freeze agents such as sugars, urea, ethylene glycol propylene glycol and rheological additives such as finely divided attapulgite clay, magnesium aluminates, bentonites, hectorites, colloidal silicic acid, heteropolysaccharides and microcrystalline cellulose.

The PDMS preferably has a molecular weight of from 10,000 to 400,000, more preferably from 50,000 to 200,000. The method of the invention is particularly useful when the pesticide employed is a mixed pesticide, comprising ethirimol, flutriafol and thiabendazole, such as that sold under the Trade Mark FERRAX, and with aqueous liquid seed treatments containing phenyl mercury acetate, guazatine, triacetate, myclobutanil or a mixture thereof. Pesticidal materials which are useful in the method of the present invention also include:

| | |
|---|---|
| Anthraquinone | Benalaxyl |
| Bendiocarb | Benomyl |
| Bitertanol | Captan |
| Carbendazin | Carbophenothion |
| Carbosulphan | Carboxin |
| Cartap hydrochloride | Chlorfenvinphos |
| Chloroneb | Chlorpyrifos |
| Chlorpyrifos-methyl | Cloethocarb |
| Cuprous oxide | Cymoxanil |
| Draxoxolon | Dyfonate |
| Endulsophan | Ethirimol |
| Ethion | Etridiazole |
| Fenfuran | Fenpropimorph |
| Flutriafol | Fonofos |
| Fosetyl | Fuberidazole |
| Furathiocarb | Furmecyclox |
| Gamma-HCH | Guazatine |
| Hymexazol | Imazalil |
| Iodofenphos | Iprodione |
| Isophenophos | Metalaxyl |
| Methiocarb | Myclobutanil |
| Nuarimol | Ofurace |
| Oxadixyl | Copper oxyquinolate |
| Organo mercury compounds | Prochloraz |
| Quintozene | Thiabendazole |
| Thiophanate-methyl | Thiram |
| Triadimenol | Triforine |

Copper oxychloride and biological control agents such as *Bacillus thuringiensis*. In addition, mixtures and combinations of the above materials are within the scope of this invention.

At low levels of application employed in accordance with the invention, it is generally unnecessary to undertake a separate drying step, after application of the treatment to the seeds. In accordance with a preferred method of the invention therefore, no separate drying step is implemented but this does not preclude the employment of a drying step should other factors dictate the need for one.

The number of preferred embodiments of the invention are illustrated in the following examples.

EXAMPLE 1

|  | percent w/w |
|---|---|
| Polyethylene glycol (Mw 6000) | 5.0 |
| Antifoam agent (TM FOAMASTER UDB) | 0.02 |
| Pigment (Luconyl Red 3855) | 5.0 |
| PDMS Emulsion - (TM DOW CORNING HV490) | 2.5 |
| Water | 87.5 |

EXAMPLE 2

|  | percent w/w |
|---|---|
| Polyethylene glycol (Mw 6000) | 2.5 |
| Antifoam agent (TM FOAMASTER UDB) | 0.005 |
| Pigment (Colanyl Red FRGX) | 6.0 |
| PDMS Emulsion - (TM DOW CORNING HV490) | 2.5 |
| Water | 88.0 |

EXAMPLE 3

|  | percent w/w |
|---|---|
| Methyl Cellulose 6 percent w/w soln (TM METHOCEL A15) | 10.0 |
| Antifoam agent (TM FOAMASTER UDB) | 0.05 |
| Pigment (Irgalite Orange) | 7.0 |
| PDMS Emulsion - (TM DOW CORNING HV490) | 2.5 |
| Water | 80.5 |

EXAMPLE 4

|  | percent w/w |
|---|---|
| Polyethylene glycol (NW E6000) | 2.5 |
| Antifoam agent (TM FOAMASTER UDB) | 0.02 |
| Pigment (Luconyl) | 5.0 |
| Propylene glycol | 10.0 |
| PDMS Emulsion - (TM DOW CORNING HV490) | 2.5 |
| Water | 80.0 |

EXAMPLE 5

|  | percent w/w |
|---|---|
| Methyl Cellulose 6 percent w/w soln (TM METHOCEL E5) | 15.0 |
| Antifoam agent (TM FOAMASTER UDB) | 0.02 |
| Urea | 10.0 |
| Pigment (Irgalite Orange F2G-PI) | 7.0 |
| PDMS Emulsion - (TM DOW CORNING HV490) | 2.5 |
| Water | 65.48 |

EXAMPLE 6

|  | percent w/w |
|---|---|
| Methyl Cellulose 6 percent w/w soln (TM METHOCEL E5) | 15.0 |
| Antifoam agent (TM FOAMASTER UDB) | 0.02 |
| Urea | 10.0 |
| Pigment (Monastral Green GNE-HD) | 6.0 |
| PDMS Emulsion - (TM DOW CORNING HV490) | 2.5 |
| Water | 66.48 |

EXAMPLE 7

|  | percent w/w |
|---|---|
| Methyl Cellulose 6 percent w/w soln (TM METHOCEL E5 premium) | 15.0 |
| Antifoam agent (TM FOAMASTER UDB) | 0.02 |
| Urea | 10.0 |
| Pigment (Irgalite Orange F2G-PI) | 7.0 |
| PDMS Emulsion - (TM DOW CORNING HV490) | 2.5 |
| Water | 75.5 |

EXAMPLE 8

|  | percent w/w |
|---|---|
| Alkyd resin (Kelsol 3931) | 5.0 |
| PDMS Emulsion - (TM DOW CORNING HV490) | 2.5 |
| Water | 92.5 |

EXAMPLE 9

|  | percent w/w |
|---|---|
| Alkyd resin (Kelsol 3931) | 5.0 |
| PDMS Emulsion - (TM DOW CORNING HV490) | 5.0 |
| Water | 90.0 |

EXAMPLE 10

|  | percent w/w |
|---|---|
| PDMS Emulsion - (TM DOW CORNING HV490) | 2.5 |
| Water | 97.5 |

EXAMPLE 11

|  | percent w/w |
|---|---|
| PDMS Emulsion - (TM DOW CORNING HV490) | 5.0 |
| Water | 95.0 |

COMPARATIVE EXAMPLE A

The composition was the same as that of Example 1, except that the PDMS was replaced by water.

COMPARATIVE EXAMPLE B

The composition was the same as that of Example 1, except that the PDMS was replaced by a polyethylene wax-(TM POLYMUL MS40).

COMPARATIVE EXAMPLE C

The composition was the same as that of Example 1, except that the PDMS was replaced by a calcium stearate dispersion (TM NOPCOL 1097-A).

COMPARATIVE EXAMPLE D

The composition was the same as that of Example 1, except that the PDMS was replaced by a polytetrafluoroethylene dispersion - (TM TEFLON 852-201).

COMPARATIVE EXAMPLE E

|  | percent w/w |
|---|---|
| Water | 100.0 |

Each of the compositions of Examples 1, 2 and 3 was applied to wheat, simultaneously with a commercial seed treatment containing phenyl mercury acetate. The compositions were applied through separate pipework to a rotary atomizing disc at application rates of 0.4 percent by weight (based on the dry seed) of the PDMS-containing composition, and 0.1 percent by weight of the pesticide.

The relative flow rates of the treated and untreated seeds are shown below:

| | Flow |
|---|---|
| untreated wheat | 100.0 |
| pesticide alone | 100.7 |
| pesticide plus Comparative Example A | 91.9 |
| pesticide plus Comparative Example B | 99.6 |
| pesticide plus Comparative Example C | 89.7 |
| pesticide plus Comparative Example D | 92.9 |
| pesticide plus Example 1 | 105.0 |
| pesticide plus Example 1 | 108.5 |
| pesticide plus Example 2 | 103.7 |
| pesticide plus Example 3 | 103.5 |
| pesticide plus Example 4 | 101.7 |
| pesticide plus water | 94.6 |

The seed coated with pesticide alone was relatively free flowing, but produced dust. The remaining coated seeds (i.e. those coated with compositions including polyethylene glycol as a film former) were of uniform color, and pesticide distribution, and were free from dust. However, the seeds treated with the composition of the Comparative Examples (i.e. those not containing PDMS) had substantially decreased flow rates as compared with untreated wheat. The seed treated with the compositions in accordance with the invention had a flow rate which was better than that of untreated wheat.

APPLICATION OF COMPOSITIONS EXAMPLES 5 TO 11 AND COMPARATIVE EXAMPLE F

Each of the compositions of Examples 5 to 11 and Comparative Example F was applied to barley, simultaneously with a commercial seed treatment containing phenyl mercury acetate. The compositions were applied through separate atomizing spray nozzles, at application rates of 0.4 percent by weight (based on the dry seed) of the PDMS-containing composition, and 0.11 percent by weight of the pesticide.

The relative flow rates of the treated and untreated seeds are shown below:

| | Flow |
|---|---|
| untreated barley | 100.0 |
| pesticide alone | 100.4 |
| pesticide plus Example 5 | 97.6 |
| pesticide plus Example 6 | 97.8 |
| pesticide plus Example 7 | 97.6 |
| pesticide plus Example 8 | 99.3 |
| pesticide plus Example 9 | 104.6 |
| pesticide plus Example 10 | 101.8 |
| pesticide plus Example 11 | 103.0 |
| pesticide plus Example 12 | 97.9 |
| pesticide plus Comparative Example F | 97.8 |

The seed coated with pesticide alone was relatively free flowing, but grain dust was still present. The remaining coated seeds (i.e. those coated with compositions including methyl cellulose or an alkyd resin as a film former) were of uniform color, and pesticide distribution, and were free from dust. The seed treated with the compositions in accordance with the invention had a flow rate which in some cases was better than that of untreated barley.

APPLICATION OF A COMPOSITION CONTAINING BOTH PESTICIDE AND PDMS

Various PDMS-containing compositions were prepared using the recipes noted below.

EXAMPLE 12

| | percent w/w |
|---|---|
| Alkyd resin (TM KELSOL 3931) | 28.6 |
| PDMS Emulsion - (TM DOW CORNING HV490) | 57.1 |
| Water | 14.3 |

EXAMPLE 13

Example 12 was repeated, except that a 25 percent polyvinylalcohol solution (molecular weight 2,000) was substituted for the water content.

EXAMPLE 14

Example 12 was repeated, except that methyl cellulose—6 percent w/w solution (TM METHOCEL E5) was substituted for the water.

EXAMPLE 15

Example 12 was repeated, except that a 25 percent solution of sucrose laurate was substituted for the water.

EXAMPLE 16

Example 12 was repeated, except that a 25 percent solution of polyvinylpyorolidone (TM PVP K 15) was substituted for the water.

EXAMPLE 17

Example 12 was repeated, except that the amount of PDMS was reduced to 28.55 percent, the balance being made up by 28.55 percent of a polytetrafluoroethylene dispersion (TM TEFLON CLEAR COAT 852-201).

EXAMPLE 18

| | percent w/w |
|---|---|
| PDMS Emulsion - (TM DOW CORNING HV490) | 5.0 |

-continued

|  | percent w/w |
|---|---|
| Pigment (Colanyl Red) | 8.0 |
| Water | 87.0 |

EXAMPLE 19

|  | percent w/w |
|---|---|
| PDMS Emulsion - (TM DOW CORNING HV490) | 5.0 |
| Pigment (Colanyl Red) | 8.0 |
| Methyl Cellulose 6 percent w/w soln (TM METHOCEL A15) | 10.0 |
| Water | 77.0 |

COMPARATIVE EXAMPLE G

Example 13 was repeated, except that the whole of the PDMS was replaced by a polytetrafluoroethylene emulsion (TM TEFLON CLEAR COAT 852-201).

COMPARATIVE EXAMPLE H

|  | percent w/w |
|---|---|
| Methyl Cellulose 6 percent w/w soln (TM METHOCEL A15) | 10.0 |
| Pigment (Colanyl Red) | 8.0 |
| Water | 82.0 |

Two parts by volume of the compositions of each of Examples 12 to 19, and Comparative Example 6 were then combined with five parts by volume of a commercially available pesticide composition comprising ethirimol, flutriafol and thiabendazol (TM FERRAX).

The resulting compositions were applied to barley, at an application rate of 7 ml/kg seed, using a single spray head. The flow rate of the resulting treated barley was measured, and the results are shown below:

|  | Flow |
|---|---|
| untreated barley | 100.0 |
| FERRAX alone | 75.0 |
| FERRAX plus Example 13 | 87.6 |
| FERRAX plus Example 14 | 89.0 |
| FERRAX plus Example 15 | 89.4 |
| FERRAX plus Example 16 | 87.0 |
| FERRAX plus Example 17 | 87.0 |
| FERRAX plus Example 18 | 87.5 |
| FERRAX plus Comparative Example G | 80.7 |

The coated seed produced was of uniform color, distribution, and appearance. The flow of the seeds coated in accordance with the invention was significantly improved, as compared with seeds treated with FERRAX alone. The generation of dust on handling has also reduced or eliminated when ferrax was coapplied with PDMS in accordance with the invention.

Four parts by volume of the composition of Examples 18 and 19 and Comparative Example H were then combined with one part by volume of a commercially available pesticide composition comprising phenyl mercury acetate.

The resulting compositions were applied to wheat, at an application rate of 5 mL/kg, using a single spray head. The flow rate of the resulting treated wheat was measured, and the results are shown below:

|  | Flow |
|---|---|
| untreated wheat | 100.0 |
| pesticide alone | 98.1 |
| pesticide plus Example 18 | 114.2 |
| pesticide plus Example 19 | 126.2 |
| pesticide plus Comparative Example H | 71.8 |

The coated seed produced was of uniform color, distribution, and appearance. The flow of the seeds coated in accordance with the invention was significantly improved, as compared with seeds untreated with pesticide alone.

EXAMPLE 20

|  | g/L |
|---|---|
| Guazatine triacetate | 120 |
| Ethylene glycol | 150 |
| Dye (Rhodamine B Liquid) | 7 |
| Silicon antifoam (TM FOAMASTER UDB) | 1 |
| Polyethylene glycol Mw 6000 | 42.4 |
| PDMS Emulsion - (TM DOW CORNING HV490) | 21.2 |
| Pigment (Luconyl Red 3855) | 21.2 |
| Water | Balance |

EXAMPLE 21

|  | g/L |
|---|---|
| Myclobutanil (hydrogen sulphate salt) | 30.0 |
| Guazatine triacetate | 120.0 |
| Imazalil | 14.3 |
| Dipropyleneglycol monomethyl ether (DOWANOL DPM) | 40.0 |
| Dye (Rhodamine B Liquid) | 20.0 |
| Methyl Cellulose 6 percent solution (TM METHOCEL E5) | 112.5 |
| PDMS (TM DOW CORNING HV490) | 21.2 |
| FOAMASTER UDB | 1.0 |
| Pigment (Irgalite Orange F2G-PI) | 28.0 |
| Acetic Acid | 28.0 |
| Water | Balance |

The composition of Examples 20 was applied to wheat and Example 21 was applied to barley, at an application rate of 5 mL/kg.

The resultant seeds were of uniform color, distribution and appearance with dust almost entirely eliminated.

EXAMPLE 22

|  | percent w/w |
|---|---|
| Polyethylene glycol (Mw 6000) | 2.5 |
| FOAMASTER UDB Antifoam | 0.02 |
| PDMS (TM DOW CORNING HV490) | 2.5 |
| Pigment (Luconyl Red) | 1.25 |
| Water | Balance |

COMPARATIVE EXAMPLE I

The composition was the same as Example 22 except the PDMS was replaced by water.

EXAMPLE 23

| | percent w/w |
|---|---|
| Alkyd resin (Kelsol 3931) | 23.5 |
| PDMS (TM DOW CORNING HV490) | 47.0 |
| Pigment (Luconyl Red) | 6.0 |
| Poligen WE1 (film forming copolymer) | 11.75 |
| Water | Balance |

The compositions of Examples 22 and 23 and Comparative Example I were coapplied with seed treatment formulations A, B, and C (identified below) to wheat, all at application rates of 2 mL/kg (total).

Formulation A is an aqueous suspension concentrate seed treatment containing 22.5 g/L fuberidzole and 187.5 g/L triadimenol.

Formulation B is an aqueous suspension concentrate and treatment containing 100 g/L copper oxquinolate (Betaxate) and 250 g/L anthraquinone.

Formulation C is an aqueous liquid seed treatment containing 300 g/L guazatine tri-acetate.

The flow rates of the resulting treated wheat was measured and the result are shown below:

| Composition | ml/Kg application rate | Flow |
|---|---|---|
| Untreated wheat | — | 100.0 |
| Formulation A | 2 + 2 ml water | 68.0 |
| Formulation A plus Example 23 | 2 | 85.6 |
| Formulation A plus Example 22 | 2 | 85.6 |
| Formulation B | 2 + 6 ml water | 78.3 |
| Formulation B plus Comparative Example I | 2 + 4 ml water | 75.8 |
| Formulation B plus Example 23 | 2 + 4 ml water | 89.9 |
| Formulation C | 2 | 90.4 |
| Formulation C plus Example 22 | 2 | 101.1 |

Again, the coated seed produced was of uniform color distribution, and appearance. The flow of the seeds coated in accordance with the invention was significantly improved, as compared with the seeds treated with pesticide alone.

Germination trials were samples of wheat and barley with the coatings of the invention applied with both phenylmercury acetate and FERRAX showed the coatings had no adverse effects on the germination and growth of the seeds compared to seeds treated with pesticide alone.

What is claimed:

1. A method for treating plant seeds with a pesticide and improving the bulk flow properties thereof, which comprises applying to said seeds and effective amount of a pesticidal substance and from 0.001 to 2.0 percent, based on the untreated weight of the seeds, of a lubricant which is non-crosslinked polydimethylsiloxane, and which is applied to the seeds as an aqueous emulsion thereof.

2. A method as claimed in claim 1 comprising applying the pesticidal substance and the polydimethylsiloxane to the seeds simultaneously.

3. A method as claimed in claim 2 wherein the pesticidal substance and the polydimethylsiloxane are applied in the form of a composition comprising, from 1.0 to 30 percent by weight of a pesticidal substance, and from 2 to 30 percent by weight of the polydimethylsiloxane.

4. A method as claimed in claim 2 wherein the pesticidal substance and the polydimethylsiloxane are co-applied to the seeds from separate compositions.

5. A method as claimed in claim 1 wherein the polydimethylsiloxane is applied to seeds to which the pesticidal substance has been previously applied.

6. A method as claimed in claim 5 wherein the polydimethylsiloxane is applied in the form of an aqueous emulsion composition containing a coloring agent.

7. A method as claimed in claim 5 wherein the polydimethylsiloxane is applied in the form of an aqueous emulsion composition comprising a film forming polymer.

8. A method as claimed in claim 7, wherein the film-forming polymer is selected from the group consisting of a polyethylene glycol, an alkyd resin, a polyvinyl alcohol, a polyvinyl pyrrolidone, a polyvinyl pyrrolidone/vinyl acetate copolymer, a styrene or ethylene/acrylic acid copolymer, a methyl cellulose, a film forming latex, a sucrose ester, an ethyl cellulose or hydroxypropyl cellulose, a maleic anhydride/vinyl ether copolymer, a polyacrylate and a polymethacrylate.

9. A method as claimed in claim 5, wherein the polydimethylsiloxane has a molecular weight of from 10,000 to 400,000.

10. A method as claimed in claim 1, wherein the pesticidal substance is selected from the group consisting of ethirimol, flutriafol, thiabendazol, a phenyl mercury acetate, guazatine, triacetate, myclobutanil and a mixture of two or more thereof.

* * * * *